United States Patent
Onuma et al.

(10) Patent No.: US 10,219,932 B2
(45) Date of Patent: Mar. 5, 2019

(54) PROTECTION GARMENT

(71) Applicants: OKAMOTO CORPORATION, Kitakatsuragi-gun, Nara (JP); THE RITSUMEIKAN TRUST, Kyoto-shi, Kyoto (JP)

(72) Inventors: Nobuaki Onuma, Nara (JP); Chika Sokawa, Nara (JP); Masaaki Makikawa, Shiga (JP)

(73) Assignees: OKAMOTO CORPORATION, Nara (JP); THE RITSUMEIKAN TRUST, Kyoto (JP)

( * ) Notice: Subject to any disclaimer, the term of this patent is extended or adjusted under 35 U.S.C. 154(b) by 481 days.

(21) Appl. No.: 14/934,218

(22) Filed: Nov. 6, 2015

(65) Prior Publication Data
US 2016/0206465 A1   Jul. 21, 2016

(30) Foreign Application Priority Data
Jan. 15, 2015 (JP) ................... 2015-006241

(51) Int. Cl.
*A61F 5/01* (2006.01)

(52) U.S. Cl.
CPC .......... *A61F 5/0118* (2013.01); *A61F 5/0123* (2013.01)

(58) Field of Classification Search
CPC .... A61F 5/0118; A61F 5/0123; A61F 5/0106; A61F 5/01; A61F 5/0109
See application file for complete search history.

(56) References Cited

U.S. PATENT DOCUMENTS

| 3,046,981 | A | * | 7/1962 | Biggs, Jr. | A61F 5/0109 602/26 |
| 4,366,813 | A | * | 1/1983 | Nelson | A61F 5/0109 2/24 |
| 4,706,302 | A | | 11/1987 | Padfield | |
| 4,791,916 | A | * | 12/1988 | Paez | A61F 5/0123 602/26 |
| 4,940,044 | A | * | 7/1990 | Castillo | A61F 5/0123 602/16 |
| 5,267,951 | A | * | 12/1993 | Ishii | A61F 13/061 602/14 |

(Continued)

FOREIGN PATENT DOCUMENTS

| JP | 10286275 A | 10/1998 |
| JP | 2007500586 A | 1/2007 |

(Continued)

OTHER PUBLICATIONS

1st Office Action for JP 2015-006241, dated Sep. 25, 2018, and English language translation thereof.

*Primary Examiner* — Tarla R Patel
(74) *Attorney, Agent, or Firm* — Kristina Castellano; Castellano PLLC

(57) ABSTRACT

A supporter according to the present invention includes a first supporting section provided so as to extend along a lateral side of a knee joint, a second supporting section extending diagonally upwardly from a first long side along an upper edge of a kneecap so as to reach a second long side, and a third supporting section extending diagonally downwardly from the first long side along a lower edge of the kneecap so as to reach the second long side.

8 Claims, 8 Drawing Sheets

(56) References Cited

U.S. PATENT DOCUMENTS

| | | | | |
|---|---|---|---|---|
| 5,512,039 A * | 4/1996 | White | ............... | A61F 5/0106 602/26 |
| 6,592,539 B1 | 7/2003 | Einarsson | | |
| 7,662,122 B2 * | 2/2010 | Sterling | ............... | A61F 5/0123 128/882 |
| 7,959,591 B2 | 6/2011 | Powers | | |
| 8,852,133 B2 | 10/2014 | Paulos | | |
| 2004/0153017 A1 | 8/2004 | Simmons | | |
| 2004/0176715 A1 * | 9/2004 | Nelson | ............... | A61F 5/0106 602/26 |
| 2006/0094999 A1 | 5/2006 | Cropper | | |
| 2006/0130215 A1 | 6/2006 | Torry | | |
| 2006/0264793 A1 | 11/2006 | Simmons | | |
| 2014/0243723 A1 | 8/2014 | Yamamoto | | |

FOREIGN PATENT DOCUMENTS

| | | |
|---|---|---|
| JP | 2008106404 | 5/2008 |
| JP | 2010240022 | 10/2010 |
| JP | 2011038230 A | 2/2011 |
| JP | 2012012722 A | 1/2012 |
| JP | 2012154007 A | 8/2012 |
| JP | 2016084570 | 5/2016 |
| KR | 20090085758 A | 8/2009 |
| WO | 1985000102 A1 | 1/1985 |
| WO | 19880000819 A1 | 2/1988 |
| WO | 1994000082 A1 | 1/1994 |
| WO | 2013021743 | 2/2013 |
| WO | 2014184459 A1 | 11/2014 |

\* cited by examiner

PROTECTION GARMENT

CROSS REFERENCE TO RELATED APPLICATION

This application claims priority to Japanese Patent application 2015-006241 filed on Jan. 15, 2015, the contents of which are incorporated herein by reference.

This Nonprovisional application claims priority under 35 U.S.C. § 119 on Patent Application No. 2015-006241 filed in Japan on Jan. 15, 2015, the entire contents of which are hereby incorporated by reference.

TECHNICAL FIELD

The present invention relates to a protection garment for stabilizing, in particular, an elbow or a knee. More specifically, the present invention relates to a protection garment which guides an elbow joint or a knee joint in a predetermined direction.

BACKGROUND ART

An iliotibial band which covers a lateral side of a thigh extends from an iliac crest, located in an upper end portion of an ilium constituting a pelvis, to the vicinity of an upper end of a tibia, via which a knee and an ankle are connected. The iliotibial band stabilizes a knee joint. When the knee joint extends, the iliotibial band is located in front of a lateral epicondyle of a femur. Meanwhile, when the knee joint flexes, the iliotibial band moves to behind the lateral epicondyle of the femur. In a case where the knee joint is lightly flexed, the tibia may inwardly rotate and thus an excessive stress may be applied to the iliotibial band. In such a case, the iliotibial band and the lateral epicondyle of the femur press each other and cause friction therebetween. This causes the iliotibial band syndrome.

As a specific example of the iliotibial band syndrome, there is known a symptom called a runner's knee, which occurs as a result of a running exercise. That is, a running motion from landing to kicking causes varus (a twist in an outward direction) of the knee joint. The varus of the knee joint then causes the iliotibial band and the lateral epicondyle of the femur to press each other and/or cause friction therebetween, which results in the iliotibial band syndrome. As a measure against the iliotibial band syndrome, there has been known a protection garment for guiding the knee joint in a valgus direction (inwardly).

A pes anserinus, located in a lower portion of a knee, refers to a portion to which sartorius tendon, gracilis tendon, and semitendinosus tendon, each located near a medial side of the tibia, are attached in a fan-like manner. The pes anserinus may develop pes anserine bursitis, which is an inflammation occurred in the portion to which the tendons are attached or in an anserine bursa. The pes anserine bursitis occurs (i) in a case where a pulling force of hamstrings repeatedly acts on the pes anserinus or (ii) in a case where, due to flexing and extending of the knee, friction is repeatedly caused between the pes anserinus and anterior fibers of an accessory ligament located in a medial side of the knee. The pes anserine bursitis is a sports injury which is often found in, in particular, long-distance and short-distance runners and football players. The pes anserine bursitis causes sharp pains and pressure pains in the medial side of the knee. In some cases, the pes anserine bursitis causes a friction sound and/or swelling as a result of flexing and extending of the knee. As a measure against the pes anserine bursitis, there has been known a protection garment for guiding the knee joint in a varus direction (outwardly).

Conventionally, as a technique for guiding a knee joint in a predetermined direction, various protection garments are disclosed in Patent Literatures 1 through 3.

For example, Patent Literature 1 discloses a knee supporter for correcting a varus deformity of a knee joint. This supporter is intended to correct the varus deformity in the following manner. That is, while a main body section of the supporter is wound around a knee joint, a head of a fibula displaced to the lateral side due to the varus deformity is pressed toward the medial side with use of a belt-shaped section held by the main body section.

Patent Literature 2 discloses a supporter for protecting an elbow or a knee from excessive inward turning or excessive valgus. This supporter includes a main body covering an elbow or a knee, and a supporting section provided so as to be integrated with the main body. The supporting section includes a fitting section which fits on a knee or an elbow, anchor sections respectively provided on upper and lower sides of the fitting section, and a connecting section which connects the fitting section with at least one of the anchor sections. With this supporter, the anchor section and the fitting section are connected with each other via the connecting section, thereby reducing displacement of an elbow or a knee toward a trunk with respect to a limb axis.

Patent Literature 3 discloses a knee supporter for correcting and reducing inward or outward turning of a knee joint. This supporter includes a supporter main body section covering a knee joint, and a strap which is wound on an outer surface of the supporter main body in a helical shape while pulling in an opposite direction to the direction of inward turning of the knee joint. Further, a protrusion which makes contact with the medial side of a tibia below a knee when the supporter is worn is provided on an inner surface of the supporter main body section or on an inner surface of the strap.

CITATION LIST

Patent Literature

[Patent Literature 1]
Japanese Patent Application Publication, Tokukai, No. 2010-240022 A (Publication Date: Oct. 28, 2010)
[Patent Literature 2]
Japanese Patent Application Publication, Tokukai, No. 2008-106404 A (Publication Date: May 8, 2008)
[Patent Literature 3]
WO 2013/021743 (Publication Date: Feb. 14, 2013)

SUMMARY OF INVENTION

Technical Problem

However, the above conventional techniques have the following problems. That is, according to Patent Literature 1, positional displacement of the supporter is likely to occur while the supporter is worn. Thus, it is impossible to continuously obtain a suitable effect of guiding the knee joint in the valgus direction by the supporter.

According to Patent Literature 2, the fitting section around an olecranon or around a kneecap is connected with the anchor section. This provides an effect of reducing displacement of the joint to a certain extent. However, this cannot bring about the effect of guiding the displaced joint, which effect is required for treatment of the sports injury.

According to Patent Literature 3, the strap, which is separated from the supporter main body, is wound on the outer surface of the supporter main body section. This increases a thickness of the supporter as a whole, which makes it difficult to put on and take off the supporter.

The present invention is made in view of the above problems. An object of the present invention is to provide a protection garment, such as a supporter, (i) that is able to reduce its positional displacement which may occur while the protection garment is worn, (ii) that continuously provides an excellent effect of guiding a joint, and (iii) that is easy to put on and take off.

Solution to Problem

In order to attain the above object, a protection garment according to the present invention is a protection garment including: a first supporting section (i) extending in a longitudinal direction of a leg (lower limb) which is to wear the protection garment and (ii) being provided along a medial side or a lateral side of a knee joint of the leg; a second supporting section extending diagonally upwardly from a first long side, which is one of two facing long sides of the first supporting section, along an upper edge of a kneecap of the leg so as to reach a second long side, which is the other one of the two facing long sides of the first supporting section, in such a manner that the second supporting section surrounds a thigh of the leg, the first long side being closer to the kneecap than the second long side is; and a third supporting section extending diagonally downwardly from the first long side along a lower edge of the kneecap so as to reach the second long side in such a manner that the third supporting section surrounds a crus of the leg.

In order to attain the above object, a protection garment according to the present invention is a protection garment including: a first supporting section (i) extending in a longitudinal direction of an arm (upper limb) which is to wear the protection garment and (ii) being provided along a medial side or a lateral side of an elbow joint of the arm; a second supporting section extending diagonally upwardly from a first long side, which is one of two facing long sides of the first supporting section, along an upper edge of an olecranon of the arm so as to reach a second long side, which is the other one of the two facing long sides of the first supporting section, in such a manner that the second supporting section surrounds an upper arm of the arm, the first long side being closer to the olecranon of the arm than the second long side is; and a third supporting section extending diagonally downwardly from the first long side along a lower edge of the olecranon of the arm so as to reach the second long side in such a manner that the third supporting section surrounds a forearm of the arm.

Advantageous Effects of Invention

The present invention makes it possible to provide a protection garment (i) that is able to reduce its positional displacement which may occur while the protection garment is worn, (ii) that continuously provides an excellent effect of guiding a joint, and (iii) that is easy to put on and take off.

BRIEF DESCRIPTION OF DRAWINGS

(a) of FIG. 5 is a view for schematically illustrating a test method of Example 2, and (b)

(a) of FIG. 6 is a view for schematically illustrating a test method of Example 3, and (b)

DESCRIPTION OF EMBODIMENTS

Figure 1:
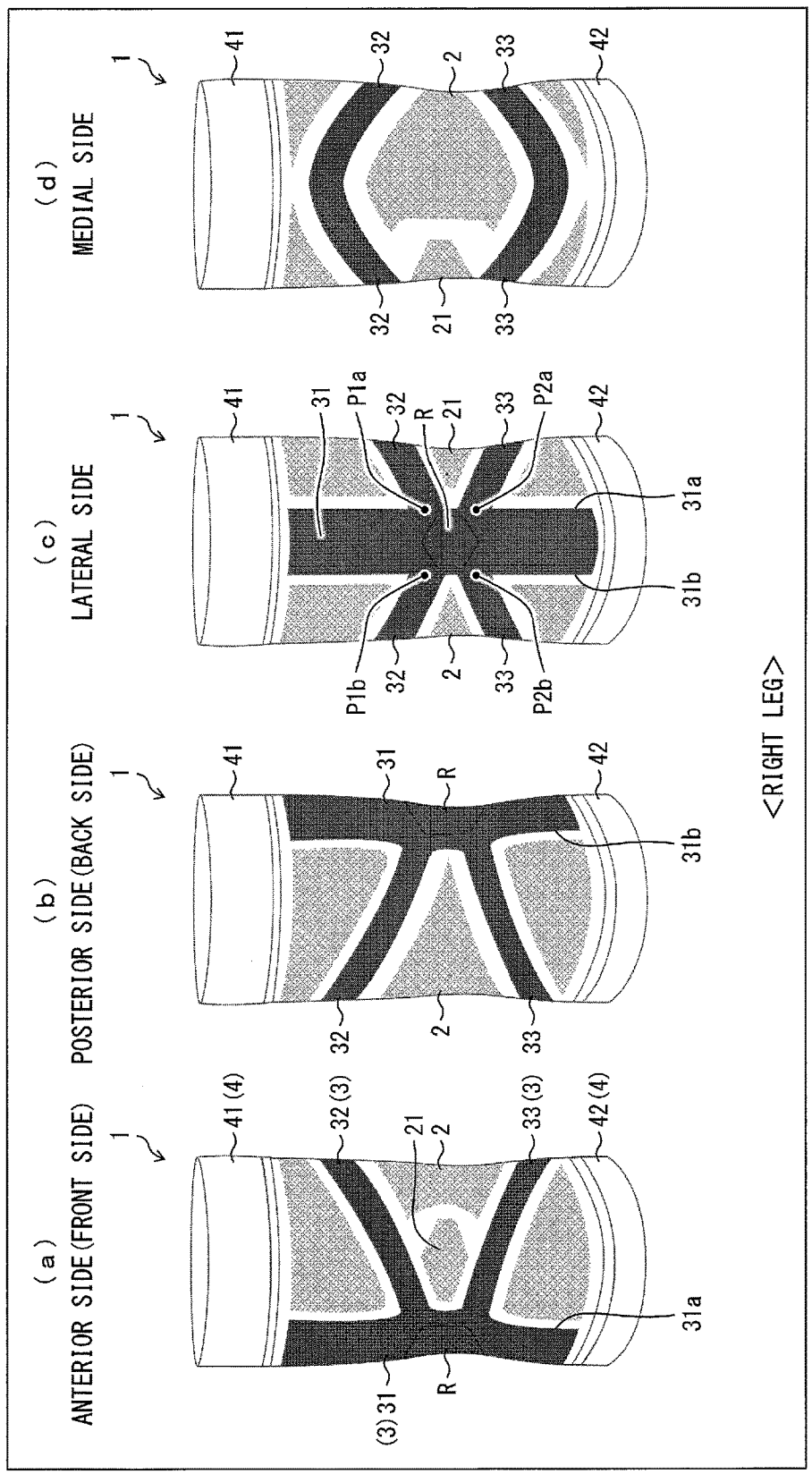
FIG. 1 is a set of diagrams (a) through (d) illustrating an appearance of a right leg supporter according to an embodiment of the present invention. (a) of FIG. 1 is a front view, (b) of FIG. 1 is a back view, (c) of FIG. 1 is a lateral side view, and (d) of FIG. 1 is a medial side view.
Figure 2:
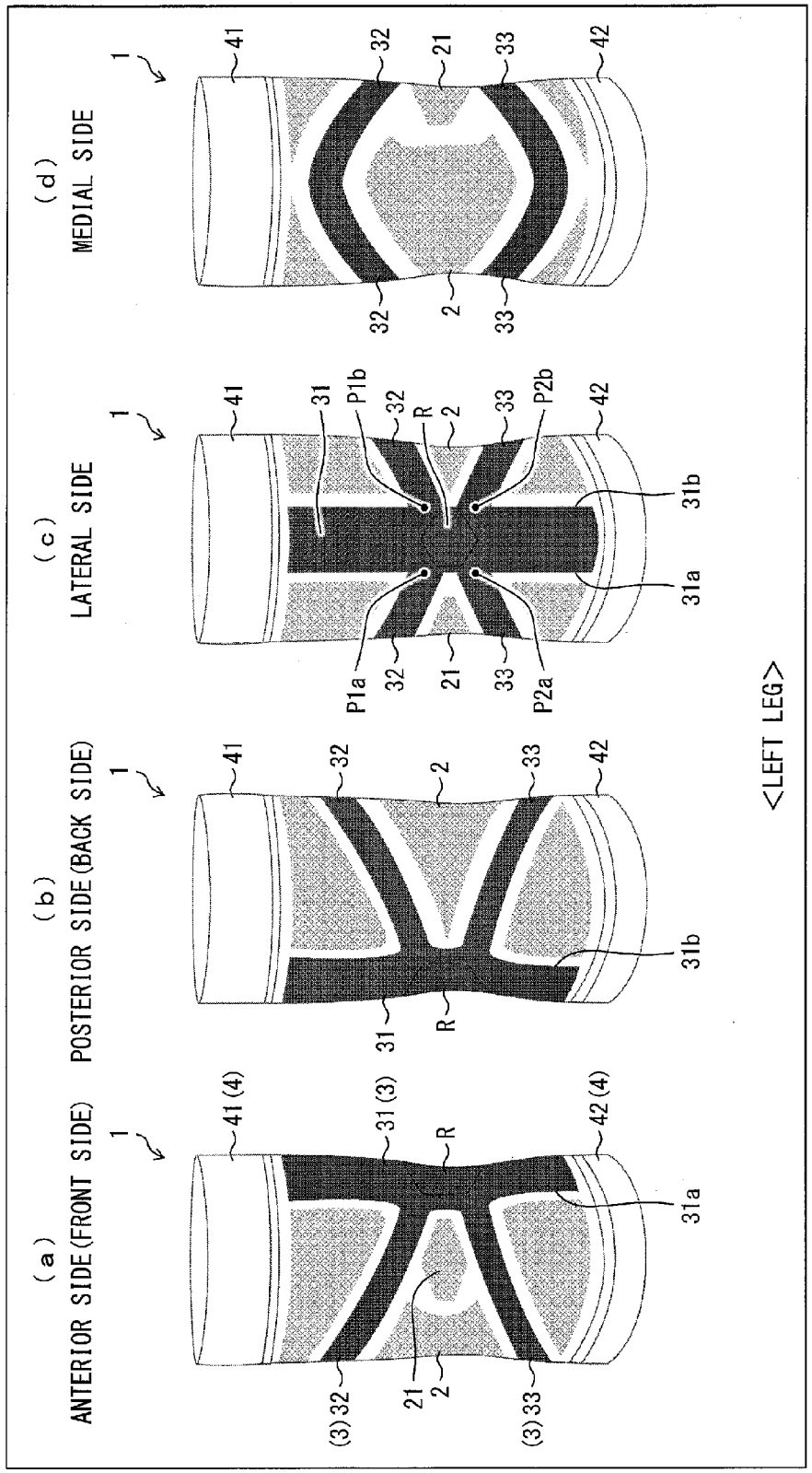
FIG. 2 is a set of diagrams (a) through (d) illustrating an appearance of a left leg supporter according to an embodiment. (a) of FIG. 2 is a front view, (b) of FIG. 2 is a back view, (c) of FIG. 2 is a lateral side view, and (d) of FIG. 2 is a medial side view.

The following discusses an embodiment of the present invention with reference to FIGS. 1 and 2. The present embodiment deals with an example in which a protection garment according to the present invention is provided as a knee supporter. However, the present invention is not limited to the knee supporter, and is also suitably applicable to an elbow supporter and to other various protection garments.

[Configuration of Supporter 1]

(a) through (d) of FIG. 1 are views illustrating an appearance of a right leg supporter 1 according to the present embodiment. Specifically, (a) of FIG. 1 is a front view, (b) of FIG. 1 is a back view, (c) of FIG. 1 is a lateral side view, and (d) of FIG. 1 is a medial side view.

(a) through (d) of FIG. 2 are views illustrating an appearance of a left leg supporter 1 according to the present embodiment. Specifically, (a) of FIG. 2 is a front view, (b) of FIG. 2 is a back view, (c) of FIG. 2 is a lateral side view, and (d) of FIG. 2 is a medial side view.

The supporter 1 according to the present embodiment is to be worn on a knee (knee joint) so that the supporter 1 guides the knee joint in a valgus direction (inwardly). The supporter 1 according to the present embodiment is used for various purposes of, for example, preventing the pes anserine bursitis, reducing pains in the knee joint, and correcting bow legs.

As illustrated in FIGS. 1 and 2, the supporter 1 includes a main body section 2, a supporting section 3, and anchor sections 4.

(Main Body Section 2)

The main body section 2 is made of cloth having stretchability, and covers at least a knee joint. The main body section partially has a mesh structure (shaded sections in FIGS. 1 and 2) so as to have excellent air permeability. In the present embodiment, the cloth of the main body section 2 is knitted by a knitting machine. Alternatively, the main body section 2 can be provided in such a manner that cloth is woven by a weaving machine and the cloth thus woven is sewed on another member which is not the main body section 2.

On a surface surrounding the main body section 2, the supporting section 3 is integrally provided. The supporting section 3 has a lower stretchability than that of the main body section 2. Further, to respective upper and lower ends of the main body section 2, the anchor sections 4 made of cloth having stretchability are integrally provided. The anchor sections 4 are formed by a circular knitting machine so that the anchor section 4 is continuous with the main body section 2.

In order to more effectively prevent slipping-down of the supporter in accordance with its use and purpose, rubber strings or the like can be inserted into the main body section 2 so as to locally enhance a tightening force of the main body section 2 as compared with those of other regions.

Note that, in the present embodiment, a direction toward the head of a user of the supporter 1 is referred to as "up/upper/upward/upwardly" and a direction toward the soles of the user is referred to as "down/lower/downward/downwardly" while the user is standing.

Further, the main body section 2 includes an identification section 21 by which a part to be located on a kneecap is visually identifiable when the supporter 1 is put on the user. Thus, based on the identification section 21, the user can visually recognize a proper position on which the supporter 1 is to be put on. This makes it easier to put on the supporter 1 in the proper position. The identification section 21 can be achieved by forming a part of the main body section 2 with, e.g., different organization, a different stitch density, and/or a different material.

(Supporting Section 3)

The supporting section 3 is lower in stretchability than the main body section 2, and reduces the varus by pressing the knee joint in the valgus direction (inwardly). The supporting section 3 is made to be low in stitch density than the main body section 2 and is tuck-stitched, so as to have low stretchability. Alternatively, the supporting section 3 can attain low stretchability by arranging the supporting section 3 with a stitch structure other than the tuck-stitching, by inserting low-stretch strings into the supporting section 3, or by applying or attaching a material such as resin to the supporting section 3. The supporting section 3 includes a first supporting section 31, a second supporting section 32, and a third supporting section 33.

The first supporting section 31 extends in a longitudinal direction (hereinafter, referred to as a "vertical direction") of a leg and is provided along a medial side or a lateral side of the knee joint (in the present embodiment, the supporting section 31 is provided along the lateral side). By providing the first supporting section 31 which extends in the vertical direction along the inner side or the outer side of the knee joint, it is possible to suitably reduce positional displacement of the supporter 1.

The first supporting section 31 has two long sides facing each other, i.e., a first long side 31a and a second long side 31b. The first long side 31a is a long side located relatively on a kneecap side (i.e., an anterior side of the knee joint), and the second long side 31b is a long side facing the first long side 31a (i.e., the second long side 31b is located relatively on a posterior side of the knee joint).

The second supporting section 32 diagonally upwardly pulls a first junction (junction) P1a and a second junction (junction) P1b, at each of which the second supporting section 32 joins with the first supporting section 31 located on the lateral side of the knee joint. The second supporting section 32 is provided so as to extend diagonally upwardly from the first supporting section 31 along an upper edge of the kneecap in such a manner that the second supporting section 32 surrounds a thigh.

Specifically, the second supporting section 32 is provided such that (i) one of two ends of the second supporting section 32 joins with the first junction P1a at a certain angle and (ii) the other one of the two ends of the second supporting section 32 joins with the second junction P1b at a certain angle. The first junction P1a is located in the first long side 31a of the first supporting section 31, the second junction P1b is located in the second long side 31b of the first supporting section 31, and the first junction P1a and the second junction P1b face each other. Thus, the second supporting section 32 surrounds the thigh in such a manner that the second supporting section 32 (i) extends diagonally upwardly from the first junction P1a in the first long side 31a along the upper edge of the kneecap so as to reach a medial side of the thigh and then (ii) extends diagonally downwardly from the medial side of the thigh so as to reach the second junction P1b in the second long side 31b.

The second supporting section 32 keeps a width of about 1.8 cm constantly in a state in which the supporter 1 is not worn. In order to maintain an effective pulling force of the second supporting section 32, it is preferable that the second supporting section 32 have a width of 1.5 cm or greater in a state in which the supporter 1 is not worn. However, an excessively large width of the second supporting section 32 may cause an unnecessarily great pressure, thereby (i) making the user uncomfortable while wearing the supporter and/or (ii) disturbing movement of the knee joint.

By arranging the second supporting section 32 in this manner, the second supporting section 32 is able to diagonally upwardly pull the first junction P1a and the second junction P1b, each located on the lateral side of the knee joint.

The third supporting section 33 diagonally downwardly pulls a third junction (junction) P2a and a fourth junction (junction) P2b, at each of which the third supporting section 33 joins with the first supporting section 31 located on the lateral side of the knee joint. The third supporting section 33 is provided so as to extend diagonally downwardly from the first supporting section 31 along a lower edge of the kneecap in such a manner that the third supporting section 33 surrounds a crus.

Specifically, the third supporting section 33 is provided such that (i) one of two ends of the third supporting section 33 joins with the third junction P2a at a certain angle and (ii) the other one of the two ends of the third supporting section 33 joins with the fourth junction P2b at a certain angle. The third junction P2a is located in the first long side 31a of the first supporting section 31, the fourth junction P2b is located in the second long side 31b of the first supporting section 31, and the third junction P2a and the fourth junction P2b face each other. Thus, the third supporting section 33 surrounds the crus in such a manner that the second supporting section 33 (i) extends diagonally downwardly from the third junction P2a in the first long side 31a along the lower edge of the kneecap so as to reach a medial side of the crus and (ii)

extends diagonally upwardly from the medial side of the crus so as to reach the fourth junction P2b in the second long side 31b.

Similarly to the second supporting section 32, the third supporting section 33 keeps a width of about 1.8 cm constantly in a state in which the supporter 1 is not worn. In order to maintain an effective pulling force of the third supporting section 33, it is preferable that the third supporting section 33 have a width of 1.5 cm or greater in a state in which the supporter 1 is not worn. However, an excessively large width of the third supporting section 33 may cause an unnecessarily great pressure, thereby (i) making the user uncomfortable while wearing the supporter and/or (ii) disturbing movement of the knee joint.

By arranging the third supporting section 33 in this manner, the third supporting section 33 is able to diagonally downwardly pull the third junction P2a and the fourth junction P2b, each located on the lateral side of the knee joint.

According to the supporter 1, (i) the first junction P1a and the second junction P1b are located on a side of a lower end of the femur, (ii) the third junction P2a and the fourth junction P2b are located on a side of an upper end of the tibia, and (iii) a pressing region R, which is surrounded by the first junction P1a, the second junction P1b, the third junction P2a, and the fourth junction P2b, is located on the lateral side of the knee joint.

That is, the pressing region R, which is surrounded by four points of the first junction P1a, the second junction P1b, the third junction P2a, and the fourth junction P2b, is provided so as to cover (i) the lateral side (side part) of the knee joint, which is a node of the femur and the tibia, and (ii) the vicinity of the lateral side of the knee joint.

This combines (i) a force with which the second supporting section 32 pulls the first junction P1a and the second junction P1b diagonally upwardly with (ii) a force with which the third supporting section 33 pulls the third junction P2a and the fourth junction P2b diagonally downwardly. The combined force acts on the pressing region R, which is surrounded by the first junction P1a, the second junction P1b, the third junction P2a, and the fourth junction P2b. As a result, the force to press the knee joint from the lateral side toward the medial side is transmitted to the knee joint more properly, which makes it possible to more appropriately guide the knee joint in the valgus direction.

In order to more suitably reduce the positional displacement of the supporter 1, it is preferable that the first supporting section 31 have a width (about three times) greater than those of the second supporting section 32 and the third supporting section 33, and that the first supporting section 31 have a vertical length equal to or greater than a length corresponding to a distance between an upper end of the second supporting section 32 and a lower end of the third supporting section 33. This makes it possible to more effectively reduce the positional displacement of the supporter 1 which may occur while the supporter 1 is worn, and to maintain the force to guide the knee joint in the valgus direction.

In the present embodiment, the first supporting section 31 has a width about three times greater than those of the second supporting section 32 and the third supporting section 33, and the first supporting section 31 has a vertical length corresponding to the distance between the upper end of the second supporting section 32 and the lower end of the third supporting section 33.

Further, it is preferable that the second supporting section 32 and the third supporting section 33 be provided so as to be substantially symmetrical (substantially plane-symmetrical) with respect a virtual plane, the virtual plane being orthogonal to a direction in which the first supporting section 31 extends and passing through a center of the kneecap (i.e., a center of the identification section 21). This makes it easier to equalize (i) the force with which the second supporting section 32 pulls the pressing region R with (ii) the force with which the third supporting section 33 pulls the pressing region R. Consequently, the pressing region R is suitably pulled from the lateral side toward the medial side of the knee joint, which makes it possible to more appropriately guide the knee joint in the valgus direction.

(Anchor Section 4)

Each of the anchor sections 4 is a tubular (circular) member whose stretchability is lower than that of the main body section 2, and fixes (fastens) the supporter 1 (the main body section 2 and the supporting section 3) to the leg. The anchor sections 4 are provided on the respective upper and lower ends of the main body section 2. The two anchor sections 4 tighten the thigh and the crus firmly, so that the supporter 1 is fixed to the leg.

The anchor sections 4 includes an upper end anchor section 41, which is provided in the upper end of the main body section 2, and a lower end anchor section 42, which is provided in the lower end of the main body section 2. Both of the upper end anchor section 41 and the lower end anchor section 42 are formed by a circular knitting machine so that the upper end anchor section 41 and the lower end anchor section 42 are contentious with the main body section 2.

The upper end anchor section 41 is provided on the upper end side of the main body section 2 and constitutes an opening. The upper end anchor section 41 tightens the thigh firmly while the supporter 1 is worn, so that the supporter 1 is fixed.

The lower end anchor section 42 is provided on the lower end side of the main body section 2 and constitutes an opening. The lower end anchor section 42 tightens the crus firmly while the supporter 1 is worn, so that the supporter 1 is fixed.

With the upper end anchor section 41 and the lower end anchor section 42, it is possible to effectively reduce the positional displacement of the supporter 1 which may occur while the supporter 1 is worn, in particular, positional displacement of the supporter 1 in the vertical direction.

Note that it is preferable that the upper end anchor section 41 has a vertical width greater than that of the lower end anchor section 42. This increases the tightening force of the upper end anchor section 41 relatively, thereby allowing the upper end anchor section 41 to reliably fix the upper end side of the main body section 2 to the thigh. This makes it difficult for the supporter 1 to slip down, which enables to more effectively reduce the positional displacement of the supporter 1 in the vertical direction.

According to the supporter 1, the upper end anchor section 41 has a width of about 8 cm, and the lower end anchor section 42 has a width of about 4 cm. However, the widths of the upper end anchor section 41 and the lower end anchor section 42 are not limited to these values. However, in a case where one of the upper end anchor section 41 and the lower end anchor section 42 has an excessively large width, this may cause an unnecessarily great pressure, thereby (i) making the user uncomfortable while wearing the supporter and/or (ii) blocking the blood flow.

Further, a slip prevention structure may be provided on inner surfaces of the upper end anchor section 41 and the lower end anchor section 42, i.e., on surfaces of the upper end anchor section 41 and the lower end anchor section 42 which surfaces make contact with the leg. The slip prevention structure may be achieved by (i) inserting slip-preventive strings into the surfaces or by (ii) attaching or applying resin to the surfaces. This makes it possible to more effectively reduce the positional displacement of the supporter 1 in the vertical direction.

[Effect Yielded by Supporter 1]

The knee changes its shape when the knee joint flexes and extends, and the supporter changes its shape in accordance with the change of the knee shape. In a case where the supporter cannot be adapted to the changes in knee shape, positional displacement of the supporter occurs in a rotational direction (circumferential direction) and a vertical direction (axial direction). Such positional displacement of the supporter may occur, for example, when the cloth of the supporter attempts to return to its original shape after being stretched during flexing of the knee joint.

In order to deal with such displacement, the supporter 1 is provided with the first supporting section 31 extending in the longitudinal direction of the leg. This reduces expansion and contraction of the cloth caused by flexing and extending of the knee joint, which makes it possible to suitably reduce the positional displacement of the supporter 1.

Assume that (i) a side of the knee joint facing a direction in which the user walks forward refers to an anterior side, (ii) a side of the knee facing a direction in which the user walks backward refers to a posterior side, (iii) a side of the knee joint facing a direction toward a vertical midline of the body refers to a medial side, and (iv) a side of the knee joint facing a direction away from the vertical midline of the body refers to a lateral side. During flexing and extending of the knee joint, the medial side or the lateral side of the knee joint has a relatively smaller area (range) in which the skin moves and thus its corresponding part of the cloth of the supporter 1 less contracts along with the flexing and extending of the knee joint, as compared with the anterior side and the posterior side of the knee joint. Thus, by providing the first supporting section 31, which extends in the longitudinal direction of the leg, so as to be located on the medial side or the lateral side of the knee joint, it is possible to more suitably reduce the positional displacement of the supporter 1.

In other words, during flexing and extending of the knee joint, the medial side or the lateral side of the knee joint has a relatively smaller area in which the skin moves and thus is less influenced by (i) the changes in the knee shape due to the flexing and extending of the knee joint and by (ii) expansion and contraction of the cloth due to the changes in the knee shape, as compared with the anterior side and the posterior side of the knee joint. Thus, by providing the first supporting section 31, which has low stretchability and extends in the vertical direction, so as to be located on the lateral side of the knee joint, it is possible to more suitably reduce the positional displacement of the supporter 1.

Thus, the present embodiment makes it possible to provide the supporter 1 (i) that is able to reduce its positional displacement which may occur while the supporter 1 is worn, (ii) that continuously provides an excellent effect of guiding a knee joint, and (iii) that is easy to put on and take off.

In the present embodiment, the first supporting section 31 and the second supporting section 32 are joined with each other at the first junction P1a and the second junction P1b, which face each other across the first supporting section 31. Further, the first supporting section 31 and the third supporting section 33 are joined with each other at the third junction P2a and the fourth junction P2b, which are located below the first junction P1a and the second junction P1b and face each other across the first supporting section 31.

However, the present embodiment is not limited to the above configuration. Alternatively, the supporter 1 can be configured such that (i) one of two ends of the second supporting section 32 and one of two ends of the third supporting section 33 are joined with the same junction in the first long side 31a of the first supporting section 31, and (ii) the other one of the two ends of the second supporting section 32 and the other one of the two ends of the third supporting section 33 are joined with the same junction in the second long side 31b of the first supporting section 31. With this configuration, it is also possible to guide the knee joint in the valgus direction by the second supporting section 32 and the third supporting section 33.

OTHER APPLICATION EXAMPLES

Application Example 1

The supporter 1 according to the present embodiment may be provided with, in a part corresponding to the medial side of the knee joint, the first supporting section 31 extending in the vertical (longitudinal) direction. Consequently, the supporter 1 is able to effectively guide the knee joint in the varus direction (outwardly).

In such a case, the supporter 1 includes: (a) a first supporting section 31 (i) extending in a longitudinal direction of a leg which is to wear the supporter 1 and (ii) being provided along a medial side of a knee joint of the leg; (b) a second supporting section 32 extending diagonally upwardly from a first long side 31a, which is one of two facing long sides of the first supporting section 31, along an upper edge of a kneecap of the leg so as to reach a second long side 31b, which is the other one of the two facing long sides of the first supporting section 31, in such a manner that the second supporting section 32 surrounds a thigh of the leg, the first long side 31a being closer to the kneecap than the second long side 31b is; and (c) a third supporting section 33 extending diagonally downwardly from the first long side 31a along a lower edge of the kneecap so as to reach the second long side 31b in such a manner that the third supporting section 33 surrounds a crus of the leg.

According to the above configuration, the knee joint is guided from the medial side toward the lateral side by the second supporting section 32 and the third supporting section 33. Thus, it possible to provide the supporter 1 that is able to effectively guide the knee joint in the varus direction.

Application Example 2

Further, the supporter 1 according to the present embodiment is not limited to the knee supporter, and is suitably provided also as an elbow supporter. That is, the supporter 1 according to the present embodiment may be provided with the first supporting section 31 in a part corresponding to a lateral side of an elbow joint. Consequently, the supporter 1 is able to effectively guide the elbow joint in a valgus direction (inwardly).

In such a case, the supporter 1 includes: (a) a first supporting section 31 (i) extending in a vertical (longitudinal) direction and (ii) being provided along a lateral side of an elbow joint; (b) a second supporting section 32 extending diagonally upwardly from a first long side 31a, which is one of two facing long sides of the first supporting section 31, along an upper edge of an olecranon so as to reach a second long side 31b, which is the other one of the two facing long sides of the first supporting section 31, in such a manner that the second supporting section 32 surrounds an upper arm, the first long side 31a being closer to the olecranon than the second long side 31b is; and (c) a third supporting section 33 extending diagonally downwardly from the first long side 31a along a lower edge of the olecranon so as to reach the second long side 31b in such a manner that the third supporting section 33 surrounds a forearm.

According to the above configuration, the elbow joint is guided from the lateral side toward the medial side by the second supporting section 32 and the third supporting section 33. Thus, it possible to provide the supporter 1 that is able to effectively guide the elbow joint in the valgus direction.

Application Example 3

Furthermore, the supporter 1 according to the present embodiment may be provided with the first supporting section 31 in a part corresponding to a medial side of the elbow joint. Consequently, the supporter 1 is also able to effectively guide the elbow joint in the varus direction (outwardly.)

In such a case, the supporter 1 includes: (a) a first supporting section 31 (i) extending in a vertical (longitudinal) direction and (ii) being provided along a medial side an elbow joint; (b) a second supporting section 32 extending diagonally upwardly from a first long side 31a, which is one of two facing long sides of the first supporting section 31, along an upper edge of an olecranon so as to reach a second long side 31b, which is the other one of the two facing long sides of the first supporting section 31, in such a manner that the second supporting section 32 surrounds an upper arm, the first long side 31a being closer to the olecranon than the second long side 31b is; and (c) a third supporting section 33 extending diagonally downwardly from the first long side 31a along a lower edge of the olecranon so as to reach the second long side 31b in such a manner that the third supporting section 33 surrounds a forearm.

According to the above configuration, the elbow joint is guided from the medial side toward the lateral side by the second supporting section 32 and the third supporting section 33. Thus, it possible to provide the supporter 1 that is able to effectively guide the elbow joint in the varus direction.

Example 1

Figure 3:
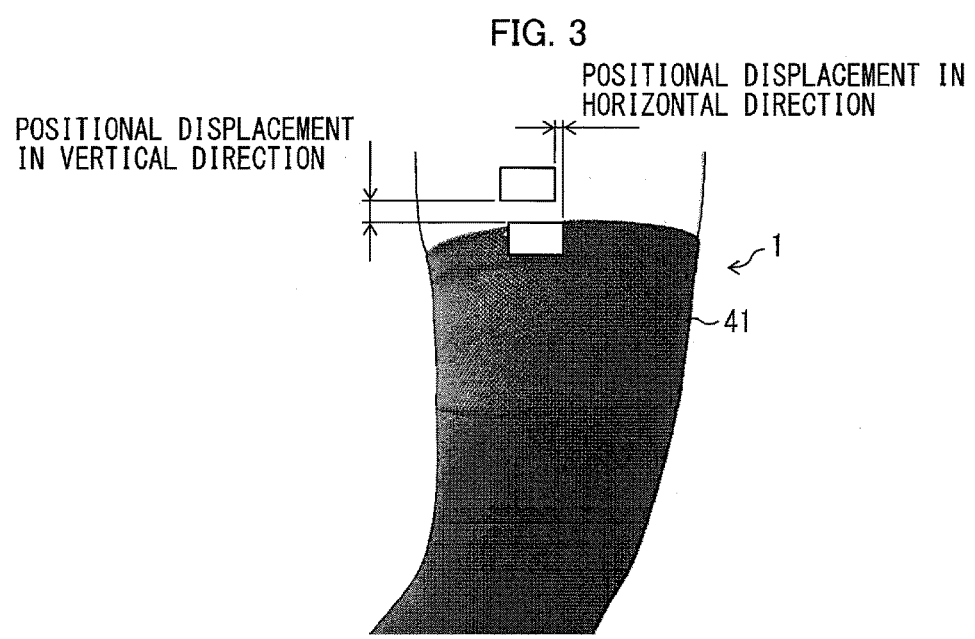
FIG. 3 is a view for schematically illustrating a test method of Example 1.
Figure 4:
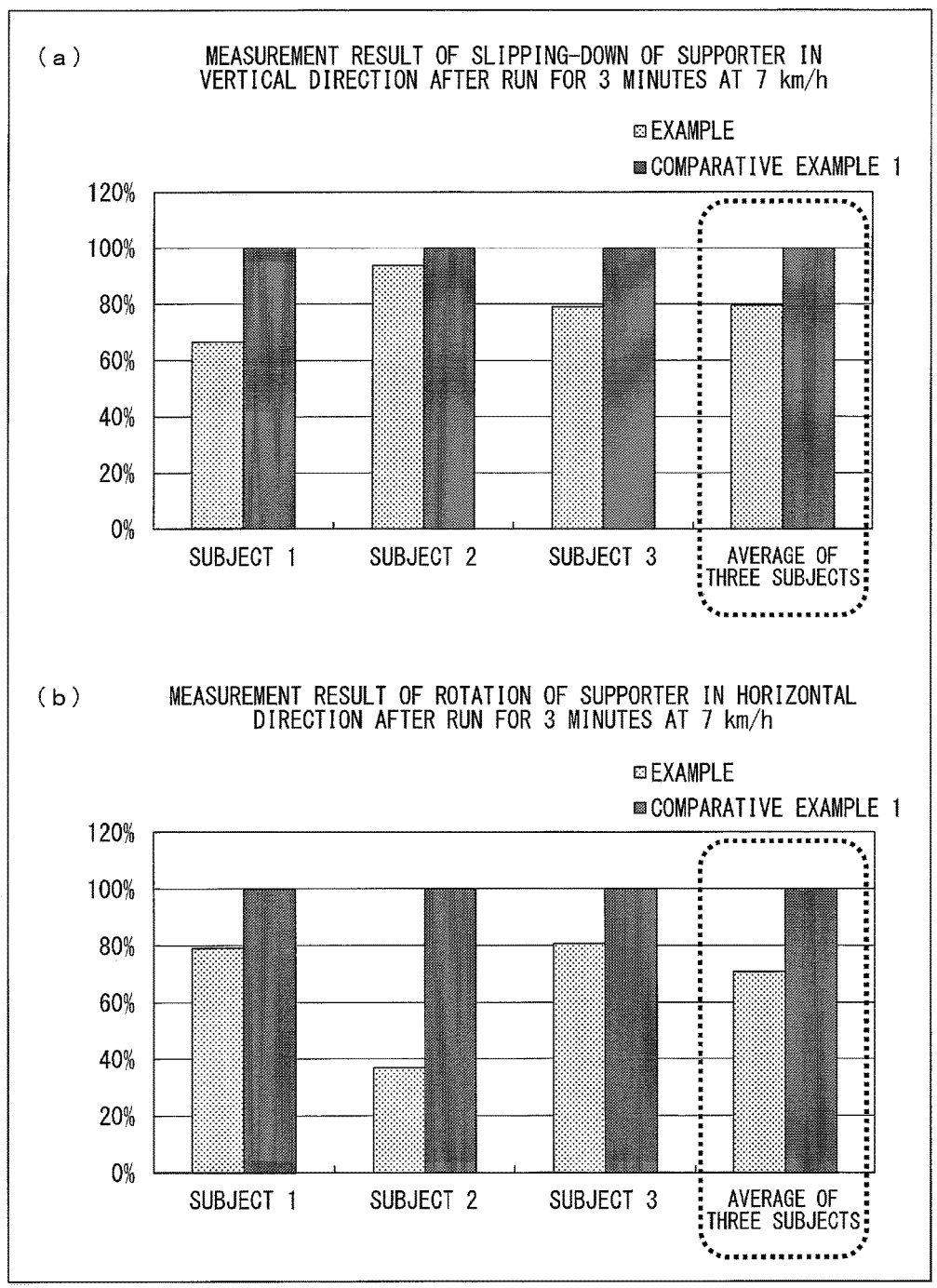
FIG. 4 shows graphs indicative of a test result of Example 1. (a) of FIG. 4 shows an amount of slipping-down in a vertical direction, and (b) of FIG. 4 shows an amount of rotational displacement in a horizontal direction.

The following discusses one example of the present invention with reference to FIGS. 3 and 4. Example 1 studied the effect of reducing the positional displacement which effect is given by the supporter 1 according to the embodiment of the present invention.

In the present example, in addition to the supporter 1 according to the embodiment of the present invention, a supporter of Comparative Example 1 not including the first supporting section 31 was prepared as a comparative subject. Namely, the supporter of Comparative Example 1 includes, as a supporting section 3, only a second supporting section 32 having a circular shape and a third supporting section 33 having a circular shape.

FIG. 3 is a view schematically illustrating a test method of the present example.

[Test Method]

(1) A subject wore supporters. As illustrated in FIG. 3, while the subject was standing, marks were given to an uppermost part of the upper anchor section 41 of each supporter and parts of each thigh (front, back, left, and right parts in the right thigh and front, back, left, and right parts in the left thigh; namely, 8 parts in total), respectively.

(2) The subject ran on a treadmill for three minutes at a speed of 7 km/h.

(3) After the run, distances from the marks on each thigh to the mark on the upper anchor section 41 were measured while the subject was standing.

[Test Result]

FIG. 4 shows graphs indicative of the test result of the present example. (a) of FIG. 4 shows an amount of positional displacement (slipping-down) in a vertical direction, and (b) of FIG. 4 shows an amount of positional displacement in a horizontal (rotational) direction. The graphs in FIG. 4 show percentages of the amounts of the positional displacement of the supporter 1 with respect to amounts (100%) of positional displacement of the supporter of Comparative Example 1. Note that each amount of the positional displacement illustrated in (a) of FIG. 4 is an average of values measured on the 8 marks.

As illustrated in (a) of FIG. 4, the test result shows a tendency that, with the supporter 1, the positional displacement in the vertical direction, i.e., positional displacement in an axial direction of the supporter 1 was decreased by an average of 20%. Further, as illustrated in (b) of FIG. 4, the test result shows a tendency that, with the supporter 1, the positional displacement in the horizontal direction (rotational) direction, i.e., positional displacement in a circumferential direction of the supporter 1 was decreased by an average of 30% or more.

Thus, the present example demonstrates that the supporter 1 yields the effect of reducing the positional displacement in the vertical direction and the horizontal direction.

Example 2

Figure 5:
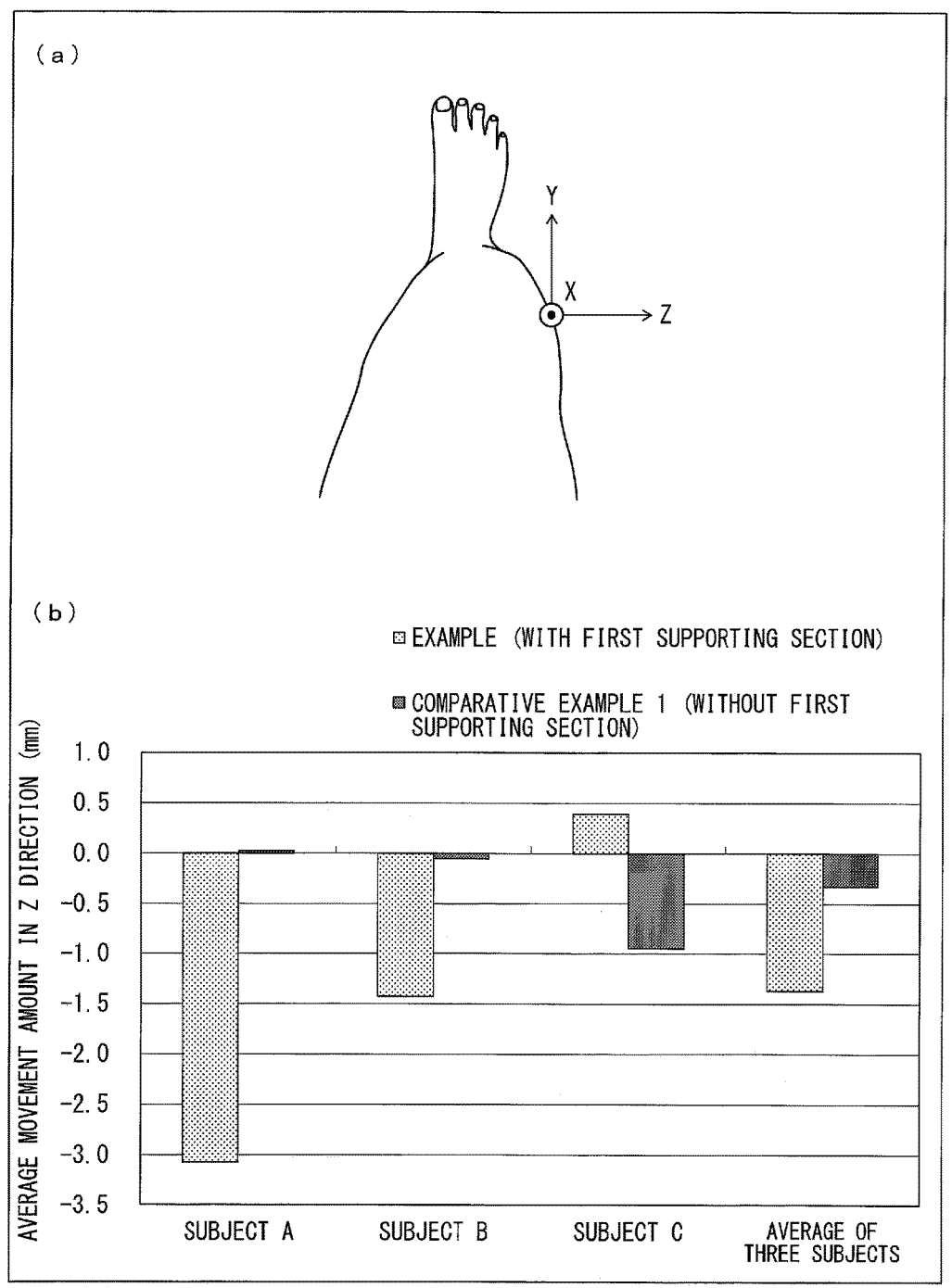
FIG. 5 is a graph showing a test result of Example 2.

The following discusses another example of the present invention with reference to FIG. 5. Example 2 studied the effect of guiding the knee joint in the valgus direction which effect is given by the supporter 1 according to the embodiment of the present invention.

With use of the supporter 1 of the embodiment of the present invention and the supporter of Comparative Example 1 used in Example 1, the present example studied how the effect of guiding the knee joint in the valgus direction varied depending on the presence or absence of the first supporting section 31.

(a) of FIG. 5 is a view for schematically illustrating a test method of the present example. (b) of FIG. 5 is a graph showing a test result of the present example.

[Test Method]

(1) As illustrated in (a) of FIG. 5, acceleration sensors were attached to lateral sides of the kneecaps of three subjects, who were adult male. Further, supporters were put on the subject so as to cover the acceleration sensors thus attached.

(2) Each of the subjects ran on a treadmill for three minutes at a speed of 7 km/h. Data was obtained for about 10 seconds during the run, and the data thus obtained was analyzed. Note that a value outputted from each acceleration sensor was measured by the mobile data recorder ZR-MDR10 (manufactured by OMRON Corporation) at a sampling frequency of 100 Hz.

(3) Comparison was made between (i) the values outputted from the acceleration sensors while the subjects wore the supporters 1 and (ii) the values outputted from the acceleration sensors while the subjects wore the supporters of Comparative Example 1.

[Test Result]

(b) of FIG. 5 shows a graph indicative of an average of movement distances in a Z direction (i.e., a direction from the knee toward the lateral side) illustrated in (a) of FIG. 5, the movement distances being calculated from the values outputted from the acceleration sensors.

In the graph in (b) of FIG. 5, a positive (+) movement amount indicates that the knee joint moved in the varus direction (outwardly), whereas a negative (−) movement amount indicates that the knee joint moved in the valgus direction (inwardly). Further, in the graph in (b) of FIG. 5, as a movement amount toward a positive side in the Z direction became smaller, movement of the knee joint in the varus direction was reduced and the knee joint was guided more in the valgus direction.

As illustrated in (b) of FIG. 5, the test result shows a tendency that the knee joints of two of the three subjects were more guided in the valgus direction while they wore the supporters 1 than while they wore the supporters of Comparative Example 1 not including the first supporting section 31.

Thus, the present example shows that the supporter 1 yields the effect of guiding the knee joint in the valgus direction.

Example 3

Figure 6:
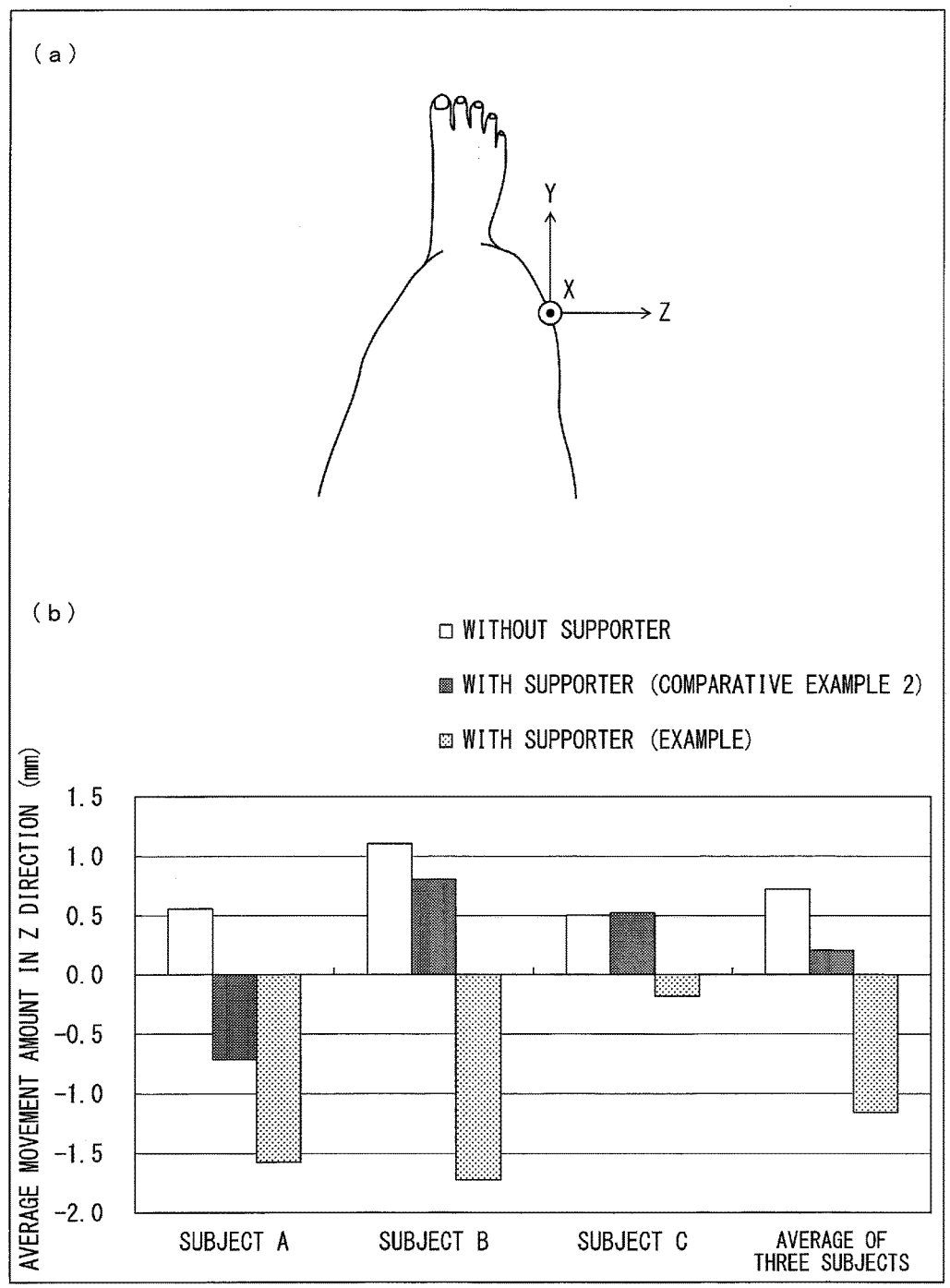
FIG. 6 is a graph showing a test result of Example 3.
Figure 7:
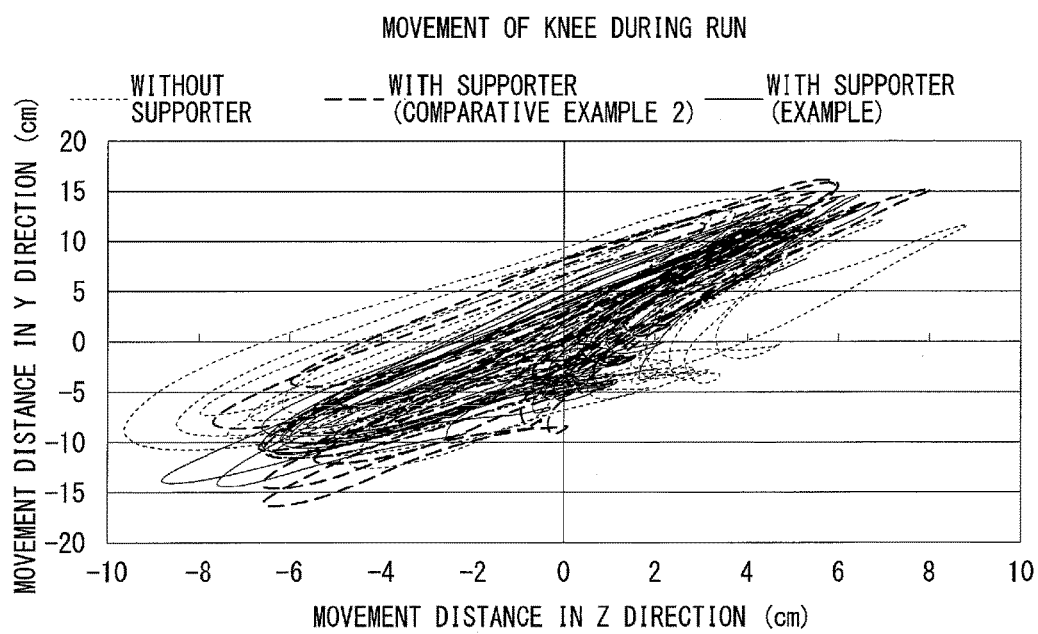
FIG. 7 is a graph showing movement tracks of a knee of a subject A in a Y-Z direction during a run in Example 3.

The following discusses still another example of the present invention with reference to FIGS. 6 and 7. With a different comparative subject and different conditions from those of Example 2, Example 3 studied the effect of guiding the knee joint in the valgus direction which effect is given by the supporter 1 according to the embodiment of the present invention.

In the present example, in addition to the supporter 1 according to the embodiment of the present invention, a supporter of Comparative Example 2 not including the supporting section 3 was prepared as a comparative subject. That is, the supporter of Comparative Example 2 is made up of the main body section 2 and the anchor section 4.

(a) of FIG. 6 is a view for schematically illustrating a test method of the present example. (b) of FIG. 6 is a graph showing a test result of Example 3.

[Test Method]

(1) Similarly to Example 2, as illustrated in (a) of FIG. 6, acceleration sensors were attached to lateral sides of the kneecaps of three subjects, who were adult male. Further, supporters were put on the subject so as to cover the acceleration sensors thus attached.

(2) Each of the subjects ran on a treadmill for three minutes at a speed of 7 km/h. Data was obtained for about 10 seconds during the run, and the data thus obtained was analyzed.

(3) Comparison was made between (i) values outputted from the acceleration sensors while the subjects did not wear any supporter, (ii) values outputted from the acceleration sensors while the subjects wore the supporters of Comparative Example 2, and (iii) values outputted from the acceleration sensors while the subjects wore the supporters 1.

[Test Result]

(b) of FIG. 6 shows a graph indicative of an average of movement distances in a Z direction (i.e., a direction from the knee toward the lateral side) illustrated in (a) of FIG. 6, the movement distances being calculated from the values outputted from the acceleration sensors.

As illustrated in (b) of FIG. 6, the test result shows a tendency that the knee joints of all the three subjects were more guided in the valgus direction while they wore the supporters 1 each including the first supporting section 31, than while they wore no supporter or while they wore the supporters of Comparative Example 2 not including the supporting section 3.

FIG. 7 is a graph showing movement tracks of a knee of a subject A in a Y-Z direction during the run in Example 3. Note that the Y direction is a direction from the knee toward the front (see (a) of FIG. 6).

As illustrated in FIG. 7, the test result shows a tendency that variation in movement tracks of the knee was reduced while the subject A wore the supporter 1, than while the subject A did not wear any supporter or while the subject A wore the supporter of Comparative Example 2 not including the supporting section 3.

Thus, the present example demonstrates that the supporter 1 yields (i) the effect of effectively guiding the knee joint in the valgus direction and (ii) the effect of stabilizing movement of the knee during a run.

[Supplemental Matters]

Figure 8:
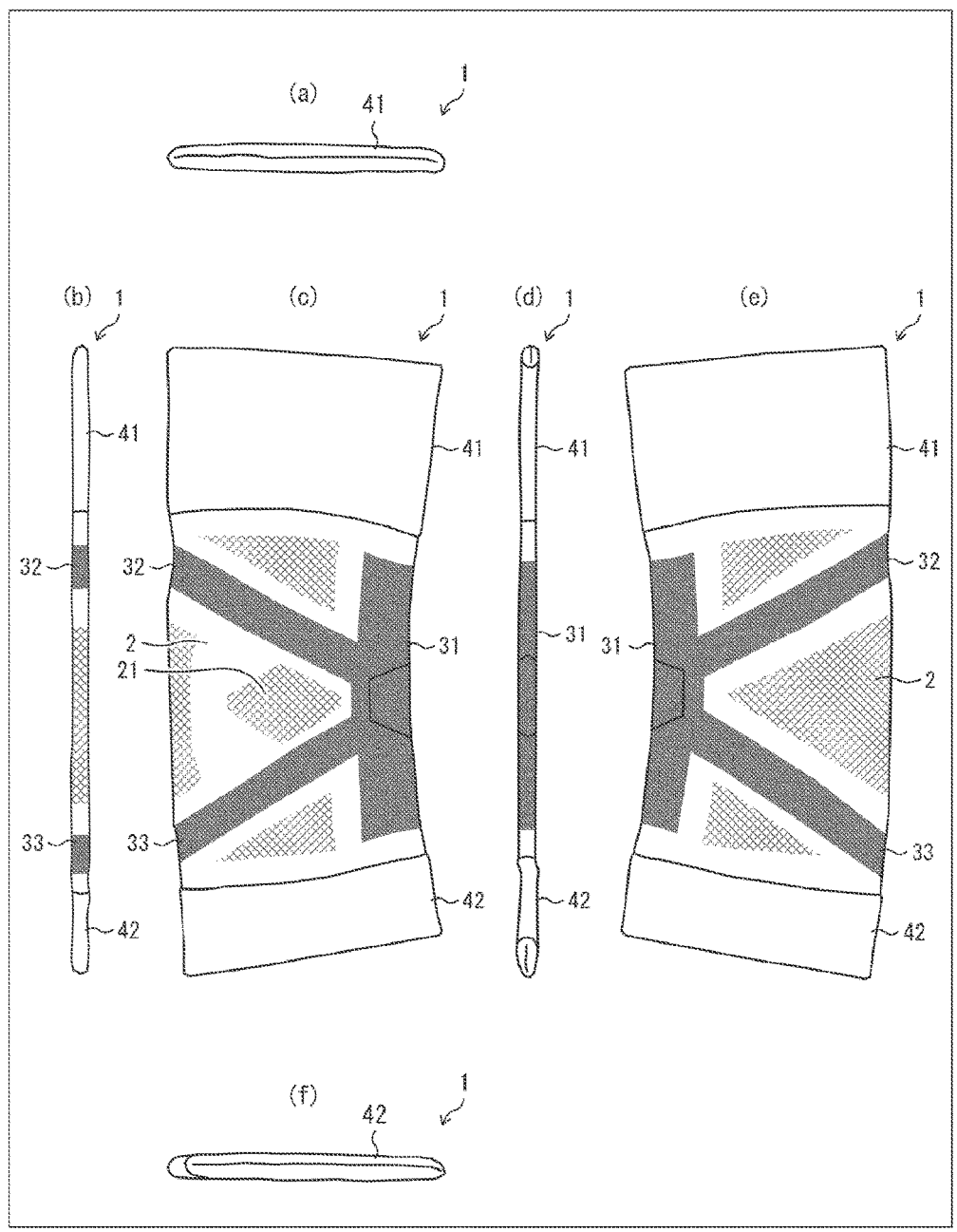
FIG. 8 is a set of photographs (drawing substitute photographs) (a) through (f) showing an appearance of a left leg supporter according to the present invention. Specifically, (a) of FIG. 8 is a photograph showing a plane surface (top surface) of the supporter, (b) of FIG. 8 is a photograph showing a side surface of the supporter which surface is for a medial side of a knee joint, (c) of FIG. 8 is a photograph showing a front surface of the supporter, (d) of FIG. 8 is a photograph showing a side surface of the supporter 1 which surface is for a lateral side of the knee joint, (e) of FIG. 8 is a photograph showing a back surface of the supporter, and (f) of FIG. 8 is a photograph showing a bottom surface of the supporter.

(a) through (f) of FIG. 8 show, for reference, an appearance of the supporter 1 according to the present embodiment. FIG. 8 is a set of photographs showing an appearance of the left leg supporter 1 according to the present invention. Specifically, (a) of FIG. 8 is a photograph showing a plane surface (top surface) of the supporter 1, (b) of FIG. 8 is a photograph showing a side surface of the supporter 1 which surface is for a medial side of a knee joint, (c) of FIG. 8 is a photograph showing a front surface of the supporter 1, (d) of FIG. 8 is a photograph showing a side surface of the supporter 1 which surface is for a lateral side of the knee joint, (e) of FIG. 8 is a photograph showing a back surface of the supporter 1, and (f) of FIG. 8 is a photograph showing a bottom surface of the supporter 1.

[Main Points]

A protection garment according to the present invention is a protection garment including: a first supporting section (i) extending in a longitudinal direction of a leg which is to wear the protection garment and (ii) being provided along a medial side or a lateral side of a knee joint of the leg; a second supporting section extending diagonally upwardly from a first long side, which is one of two facing long sides of the first supporting section, along an upper edge of a kneecap of the leg so as to reach a second long side, which is the other one of the two facing long sides of the first supporting section, in such a manner that the second supporting section surrounds a thigh of the leg, the first long side being closer to the kneecap than the second long side is; and a third supporting section extending diagonally downwardly from the first long side along a lower edge of the kneecap so as to reach the second long side in such a manner that the third supporting section surrounds a crus of the leg.

According to the above configuration, the first supporting section extending in the longitudinal direction of the leg reduces expansion and contraction of the cloth caused by flexing and extending of the knee joint, thereby making it possible to suitably reduce positional displacement of the protection garment. Assume that (i) a side of the knee joint facing a direction in which the user walks forward refers to an anterior side, (ii) a side of the knee facing a direction in which the user walks backward refers to a posterior side, (iii) a side of the knee joint facing a direction toward a vertical midline of the body refers to a medial side, and (iv) a side of the knee joint facing a direction away from the vertical midline of the body refers to a lateral side. During flexing and extending of the knee joint, the medial side or the lateral side of the knee joint has a relatively smaller area in which the skin moves and thus its corresponding part of the cloth of the protection garment less contracts along with the flexing and extending of the knee joint, as compared with the anterior side and the posterior side of the knee joint. Thus, by providing the first supporting section, which extends in the longitudinal direction of the leg, so as to be located on the medial side or the lateral side of the knee joint, it is possible to more suitably reduce positional displacement of the protection garment.

Furthermore, according to the above configuration, the second supporting section, which extends diagonally upwardly along the upper edge of the kneecap so as to surround the thigh, diagonally upwardly pulls junctions of (i) the two long sides (the first long side and the second long side) of the first supporting section and (ii) the second supporting section. In addition, according to the above configuration, the third supporting section, which extends diagonally downwardly along the lower edge of the kneecap so as to surround the crus, diagonally downwardly pulls junctions of (i) the two long sides (the first long side and the second long side) of the first supporting section and (ii) the third supporting section. Thus, a pulling force of the second supporting section in a diagonally upward direction is combined with a pulling force of the third supporting section in a diagonally downward direction, thereby making it possible to guide the knee joint in the varus direction or the valgus direction.

Since the second supporting section 2 is provided so as to surround the thigh and the third supporting section is provided so as to surround the crus, it is possible to obtain a great pulling force by the second supporting section and the third supporting section. As a result, it is possible to effectively guide the knee joint in the varus direction or the valgus direction.

For example, in a case where the first supporting section is provided on the medial side of the knee joint, the knee joint is pulled from the medial side toward the lateral side of the knee joint by the second supporting section and the third supporting section. As a result, it is possible to effectively guide the knee joint in the varus direction.

On the other hand, in a case where the first supporting section is provided on the lateral side of the knee joint, the knee joint is pulled from the lateral side toward the medial side of the knee joint by the second supporting section and the third supporting section. As a result, it is possible to effectively guide the knee joint in the valgus direction.

Further, the first supporting section, the second supporting section, and the third supporting section are formed integrally, which eliminates the need for the user to put on and take off these sections separately. This reduces time and/or effort in putting on and taking off the protection garment.

According to the above configuration, it is possible to provide a protection garment (i) that is able to reduce its positional displacement which may occur while the protection garment is worn, (ii) that provides an excellent effect of guiding a knee joint, and (iii) that is easy to put on and take off.

Note that the "pulling force in the diagonally upward direction" herein denotes a force by which a portion of the medial side or the lateral side of the knee joint is pulled toward a center of a plane which is a cross-section of the leg cut along the second supporting section. Further, the "pulling force in the diagonally downward direction" herein denotes a force by which a portion of the medial side or the lateral side of the knee joint is pulled toward a center of a plane which is a cross-section of the leg cut along the third supporting section.

The protection garment according to the present invention can be configured such that: a region of the first supporting section is provided on a side of the knee joint, the region being surrounded by (i) a junction of the first long side and the second supporting section, (ii) a junction of the second long side and the second supporting section, (iii) a junction of the first long side and the third supporting section, and (iv) a junction of the second long side and the third supporting section.

According to the above configuration, it is possible to properly press the side of the knee joint in the varus direction or the valgus direction by the region surrounded by four junctions of the first supporting section, the second supporting section, and the third supporting section. For example, by positioning the first supporting section along the lateral side of the knee joint, it is possible to press a lateral epicondyle of a femur from the lateral side of the knee joint.

Therefore, the above configuration makes it possible to more properly guide a knee joint in the varus direction or the valgus direction, which brings about an excellent effect of guiding the knee joint.

The protection garment according to the present invention can be configured such that: the first supporting section has a width greater than those of the second supporting section and the third supporting section; and the first supporting section has a length corresponding to at least a distance between (i) an upper end of the second supporting section when viewed in the longitudinal direction and (ii) a lower end of the third supporting section when viewed in the longitudinal direction.

According to the above configuration, it is possible to more effectively reduce positional displacement of the protection garment which may occur while the protection garment is worn, and to maintain, for a long term, a force to guide the knee joint in the valgus direction or the varus direction.

The protection garment according to the present invention can further include: a main body section having a tubular shape, covering at least the knee joint, and including the first supporting section, the second supporting section, and the third supporting section; and anchor sections, provided on respective upper and lower ends of the main body section, for fixing the main body section to the leg.

According to the above configuration, the anchor sections are provided on the respective upper and lower ends of the main body section having a tubular shape and including the first supporting section, the second supporting section, and the third supporting section. This makes it possible to reduce positional displacement of the protection garment which may occur while the protection garment is worn, in particular, positional displacement of the protection garment in the longitudinal direction.

Therefore, the above configuration makes it possible to more effectively reduce positional displacement of the protection garment.

The protection garment according to the present invention can be configured such that the main body section includes an identification section by which a part to be located on the kneecap is visually identifiable when the protection garment is put on the leg.

According to the above configuration, based on the identification section, the user can visually recognize a proper position on which the protection garment is to be put on.

Thus, the above configuration makes it easier to put the protection garment on the proper position, thereby improving convenience in putting on the protection garment.

The protection garment according to the present invention can be configured such that: the first supporting section, the second supporting section, the third supporting section, the main body section, and the anchor sections are knitted by a knitting machine so as to be continuous with one another; and each of the first supporting section, the second supporting section, and the third supporting section is knitted (i) with a smaller stitch than that of the main body section, (ii) with a stitch structure different from that of the main body section, or (iii) with a smaller stitch than that of the main body section and with a stitch structure different from that of the main body section, so as to be lower in stretchability in a circumferential direction than the main body section.

According to the above configuration, the members of the protection garment are formed so as to be continuous with one another. This eliminates the need for connecting the members, thereby making it possible to maintain a good production efficiency of the protection garment. Further, because the members are formed so as to be continuous with one another, unnecessary projections and depressions do not appear on the front surface and the back surface of the main body section. Thus, it is possible to provide a good wearing comfort, and this is suitable.

The protection garment according to the present invention can be configured such that the second supporting section and the third supporting section are provided so as to be substantially symmetrical with respect to a virtual plane, the virtual plane being orthogonal to a direction in which the first supporting section extends and passing through a center of the kneecap.

The above configuration makes it easier to equalize (i) the pulling force of the second supporting section provided by the junctions of (a) the two long sides (the first long side and the second long side) of the first supporting section and (b) the second supporting section with (ii) the pulling force of the third supporting section provided by the junctions of (a) the two long sides (the first long side and the second long side) of the first long side and (b) the third supporting section.

The above configuration makes it possible to more appropriately guide the knee joint in the varus direction or the valgus direction.

The protection garment of the present invention can be a supporter which is to be put on the knee joint.

According to the above configuration, it is possible to provide a supporter (i) that is able to reduce its positional displacement which may occur while the supporter is worn, (ii) that provides an excellent effect of guiding a knee joint, and (iii) that is easy to put on and take off.

A protection garment according to the present invention includes: a first supporting section (i) extending in a longitudinal direction of an arm which is to wear the protection garment and (ii) being provided along a medial side or a lateral side of an elbow joint of the arm; a second supporting section extending diagonally upwardly from a first long side, which is one of two facing long sides of the first supporting section, along an upper edge of an olecranon of the arm so as to reach a second long side, which is the other one of the two facing long sides of the first supporting section, in such a manner that the second supporting section surrounds an upper arm of the arm, the first long side being closer to the olecranon of the arm than the second long side is; and a third supporting section extending diagonally downwardly from the first long side along a lower edge of the olecranon of the arm so as to reach the second long side in such a manner that the third supporting section surrounds a forearm of the arm.

As in the case of a knee joint, the first supporting section extending in the longitudinal direction of the arm reduces expansion and contraction of the cloth caused by flexing and extending of the elbow joint, thereby making it possible to suitably reduce positional displacement of the protection garment. During flexing and extending of the elbow joint, the medial side or the lateral side of the elbow joint has a relatively smaller area in which the skin moves and thus its corresponding part of the cloth of the protection garment less contracts along with the flexing and extending of the elbow joint, as compared with the anterior side and the posterior side of the elbow joint. Thus, by providing the first supporting section, which extends in the longitudinal direction of the arm, so as to be located on the medial side or the lateral side of the elbow joint, it is possible to more suitably reduce positional displacement of the protection garment.

Furthermore, according to the above configuration, the second supporting section, which extends diagonally upwardly along the upper edge of the olecranon so as to surround the upper arm, diagonally upwardly pulls junctions of (i) the two long sides (the first long side and the second long side) of the first supporting section and (ii) the second supporting section. In addition, according to the above configuration, the third supporting section, which extends diagonally downwardly along the lower edge of the olecranon so as to surround the forearm, diagonally downwardly pulls junctions of (i) the two long sides (the first long side and the second long side) of the first supporting section and (ii) the third supporting section. Thus, a pulling force of the second supporting section in a diagonally upward direction is combined with a pulling force of the third supporting section in a diagonally downward direction, thereby making it possible to guide the elbow joint in the varus direction or the valgus direction.

Since the second supporting section 2 is provided so as to surround the upper arm and the third supporting section is provided so as to surround the forearm, it is possible to obtain a great pulling force by the second supporting section and the third supporting section. As a result, it is possible to effectively guide the elbow joint in the varus direction or the valgus direction.

For example, in a case where the first supporting section is provided on the medial side of the elbow joint, the region surrounded by four junctures of the first supporting section, the second supporting section, and the third supporting section is pulled from the medial side toward the lateral side of the elbow joint by the second supporting section and the third supporting section. As a result, it is possible to effectively guide the elbow joint in the varus direction.

On the other hand, in a case where the first supporting section is provided on the lateral side of the elbow joint, the region surrounded by four junctions of the first supporting section, the second supporting section, and the third supporting section is pulled from the lateral side toward the medial side of the elbow joint by the second supporting section and the third supporting section. As a result, it is possible to effectively guide the elbow joint in the valgus direction.

Further, the first supporting section, the second supporting section, and the third supporting section are formed integrally, which eliminates the need for the user to put on and take off these sections separately. This reduces time and/or effort in putting on and taking off the protection garment.

According to the above configuration, it is possible to provide a protection garment (i) that is able to reduce its positional displacement which may occur while the protection garment is worn, (ii) that provides an excellent effect of guiding an elbow joint, and (iii) that is easy to put on and take off.

The present invention is not limited to the description of the embodiments above, but may be altered by a skilled person within the scope of the claims. An embodiment based on a proper combination of technical means disclosed in different embodiments is encompassed in the technical scope of the present invention.

INDUSTRIAL APPLICABILITY

The present invention is suitably applicable to a protection garment for guiding an elbow joint or a knee joint in a valgus direction or a varus direction.

REFERENCE SIGNS LIST

1 Supporter (Protection Garment)
2 Main Body Section
3 Supporting Section
4 Anchor Section
21 Identification Section
31 First Supporting Section
31a First Long Side
31b Second Long Side
32 Second Supporting Section
33 Third Supporting Section
41 Upper End Anchor Section
42 Lower End Anchor Section
P1a First Junction (Junction)
P1b Second Junction (Junction)
P2a Third Junction (Junction)
P2b Fourth Junction (Junction)
R Pressing Region (Region)

The invention claimed is:

1. A protection garment comprising:
a first supporting section (i) extending in a longitudinal direction of a leg which is to wear the protection garment and (ii) being provided along a medial side or a lateral side of a knee joint of the leg;
a second supporting section extending diagonally upwardly from a first long side, which is one of two facing long sides of the first supporting section, along an upper edge of a kneecap of the leg so as to reach a second long side, which is the other one of the two facing long sides of the first supporting section, in such a manner that the second supporting section surrounds a thigh of the leg continuously around a posterior side of the thigh, the first long side being closer to the kneecap than the second long side is; and
a third supporting section extending diagonally downwardly from the first long side along a lower edge of the kneecap so as to reach the second long side in such a manner that the third supporting section surrounds a crus of the leg continuously around a posterior side of the crus;
wherein the first supporting section has a width greater than those of the second supporting section and the third supporting section; and
the first supporting section has a length corresponding to at least a distance between (i) an upper end of the second supporting section when viewed in the longitudinal direction and (ii) a lower end of the third supporting section when viewed in the longitudinal direction.

2. The protection garment as set forth in claim 1, wherein:
a region of the first supporting section is provided on a side of the knee joint, the region being surrounded by (i) a junction of the first long side and the second supporting section, (ii) a junction of the second long side and the second supporting section, (iii) a junction of the first long side and the third supporting section, and (iv) a junction of the second long side and the third supporting section.

3. The protection garment as set forth in claim 1, further comprising:
a main body section having a tubular shape, adapted for covering at least the knee joint, and including the first supporting section, the second supporting section, and the third supporting section; and
anchor sections, provided on respective upper and lower ends of the main body section, for fixing the main body section to the leg.

4. The protection garment as set forth in claim 3, wherein:
the main body section includes an identification section by which a part to be located on the kneecap is visually identifiable when the protection garment is put on the leg.

5. The protection garment as set forth in claim 3, wherein:
the first supporting section, the second supporting section, the third supporting section, the main body section, and the anchor sections are knitted by a knitting machine so as to be continuous with one another; and
each of the first supporting section, the second supporting section, and the third supporting section is knitted (i) with a smaller stitch than that of the main body section, (ii) with a stitch structure different from that of the main body section, or (iii) with a smaller stitch than that of the main body section and with a stitch structure different from that of the main body section, so as to be lower in stretchability in a circumferential direction than the main body section.

6. The protection garment as set forth in claim 1, wherein:
the second supporting section and the third supporting section are provided so as to be substantially symmetrical with respect to a virtual plane, the virtual plane being orthogonal to a direction in which the first supporting section extends and passing through a center of the kneecap.

7. The protection garment as set forth in claim 1, wherein:
the protection garment is a supporter which is to be put on the knee joint.

8. A protection garment comprising:
a first supporting section (i) extending in a longitudinal direction of an arm which is to wear the protection garment and (ii) being provided along a medial side or a lateral side of an elbow joint of the arm;
a second supporting section extending diagonally upwardly from a first long side, which is one of two facing long sides of the first supporting section, along an upper edge of an olecranon of the arm so as to reach a second long side, which is the other one of the two facing long sides of the first supporting section, in such a manner that the second supporting section surrounds an upper arm of the arm continuously around a posterior side of the upper arm, the first long side being closer to the olecranon of the arm than the second long side is; and
a third supporting section extending diagonally downwardly from the first long side along a lower edge of the olecranon of the arm so as to reach the second long side in such a manner that the third supporting section surrounds a forearm of the arm continuously around a posterior side of the forearm:;

wherein the first supporting section has a width greater than those of the second supporting section and the third supporting section; and the first supporting section has a length corresponding to at least a distance between (i) an upper end of the second supporting section when viewed in the longitudinal direction and (ii) a lower end of the third supporting section when viewed in the longitudinal direction.

* * * * *